US008822516B2

(12) United States Patent
Nisnevich et al.

(10) Patent No.: US 8,822,516 B2
(45) Date of Patent: Sep. 2, 2014

(54) PROCESS FOR THE PREPARATION OF IODIDES

(75) Inventors: Gennady Nisnevich, Haifa (IL); Mark Gandelman, Kfar-Sava (IL); Kseniya Kulbitski, Haifa (IL)

(73) Assignee: Technion Research & Development Foundation Limited, Technion, Haifa (IL)

( * ) Notice: Subject to any disclaimer, the term of this patent is extended or adjusted under 35 U.S.C. 154(b) by 0 days.

(21) Appl. No.: 13/703,183

(22) PCT Filed: Jun. 9, 2011

(86) PCT No.: PCT/IL2011/000458
§ 371 (c)(1),
(2), (4) Date: Feb. 27, 2013

(87) PCT Pub. No.: WO2011/154953
PCT Pub. Date: Dec. 15, 2011

(65) Prior Publication Data
US 2013/0165658 A1   Jun. 27, 2013

Related U.S. Application Data

(60) Provisional application No. 61/353,427, filed on Jun. 10, 2010, provisional application No. 61/427,925, filed on Dec. 29, 2010.

(51) Int. Cl.
*A01N 43/76* (2006.01)
*A61K 31/42* (2006.01)
*C07D 205/04* (2006.01)
*C07D 263/00* (2006.01)
*C07C 67/32* (2006.01)
*C07C 22/00* (2006.01)
*C07J 9/00* (2006.01)

(52) U.S. Cl.
USPC ............ 514/376; 548/230; 548/225; 548/232

(58) Field of Classification Search
USPC .......................................... 546/245; 514/376
See application file for complete search history.

(56) References Cited

U.S. PATENT DOCUMENTS

| | | | |
|---|---|---|---|
| 3,531,535 A | 9/1970 | Silbert | |
| 3,652,682 A | 3/1972 | Silbert | |
| 3,666,820 A | 5/1972 | Silbert | |
| 6,358,971 B1 | 3/2002 | Ezquerra-Carrera et al. | |
| 6,844,440 B2 | 1/2005 | Lerman et al. | |
| 7,138,555 B2 | 11/2006 | Goodbrand et al. | |
| 2009/0247795 A1 | 10/2009 | Kawakami | |
| 2010/0286152 A1 | 11/2010 | Bernasconi et al. | |
| 2013/0165658 A1 | 6/2013 | Nisnevich et al. | |

FOREIGN PATENT DOCUMENTS

| | | |
|---|---|---|
| EP | 2110369 | 10/2009 |
| IN | 803 Del 1999 | * 6/2005 |
| WO | WO2007/027917 | 3/2007 |
| WO | WO2008/098244 | 8/2008 |
| WO | WO2008/143141 | 11/2008 |
| WO | WO2008/148853 | 12/2008 |
| WO | WO2010/114179 | 10/2010 |
| WO | WO 2011/154953 | 12/2011 |
| WO | WO2012/074718 | 6/2012 |
| WO | WO2012/074732 | 6/2012 |

OTHER PUBLICATIONS

Chaykovskiy; Bulletin of the Tomsk Polytechnic University, 2007, 311, 88-90.*
Hanessian; Synthesis, 1981, 394.*
Anderson; Practical Process Research and Development, 2000, Academic Press, pp. 177, 188, 204 and 239.*
Ochiai; Journal of the American Chemical Society, 2005, 127, 12244-12245.*
Hassner; Organic Syntheses Based on Name Reactions, 2nd Edition, 2002, Elsevier, p. 410.*
Babu et al. "Synthesis and in vitro cholesterol dissolution by 23- and 24-phosphonobile acids" Steroids vol. 70, Issue 10, pp. 681-689, Sep. 2005.
Barton et al. "Investigations on the biosynthesis of morphine alkaloids" J Chem Soc. 2423-2438, (1965).
Barton et al. "The Invention of New Radical Chain Reactions-, Part VIII", Tetrahedron 41, 3901-3924. 41, 3901-3924, (1985).
Barton et al. "The Invention of new Radical Reactions. Part XVI. Radical Decarboxylative Bromination and Iodination of Aromatic Acids" Tetrahedron 43, 4321-4327, (1987).
Billotte. "Synthesis of C-Substituted Cyclic Amines Using Azacycloalkyl Organozinc Reagents" Synlett, (4): 379-380, (1998).
Bongiovanni et al. "Use of an organic base in the Zimmermann reaction" J Clin Endocrinol Metab.; 17(2):331-2. Feb. 1957.
Bordwell et al. "Synthesis of Dihalomethyl and alpha-Haloalkyl Sulfones by the Halogenative Decarboxylation of alpha-Aryl- and alpha- Alkylsulfonylalkanecarboxylic Acids" Journal of Organic Chemistry, v. 39, 2516, (1974).
Boto et al. "Synthesis of Functionalized Nitrogen Heterocycles by Radical Decarboxylation of β- and γ- Amino Acids" European Journal of Organic Chemistry Volume, Issue 4, pp. 673-682, Feb. 2005.
Chowdhury Roy. "The First Example of a Catalytic Hunsdiecker Reaction: Synthesis of beta-Halostyrenes" Journal of Organic Chemistry, vol. 62, pp. 199-200, (1997).
Collier. Product subclass 15: N-Alk-1-enylaminophosphorous compounds in Science of Synthesis,33, 565-576, (2007).
Corley et al. "Direct synthesis of 4-arylpiperidines via palladium/copper(I)-cocatalyzed Negishi coupling of a 4-piperidylzinc iodide with aromatic halides and triflates" J Org Chem. 69(15):5120-3. Jul. 23, 2004.

(Continued)

*Primary Examiner* — John Mabry
*Assistant Examiner* — Daniel Carcanague
(74) *Attorney, Agent, or Firm* — Pearl Cohen Zedek Latzer Baratz LLP

(57) ABSTRACT

This invention is directed to a process for the preparation of high yield alkyl or aryl iodide from its corresponding carboxylic acid using N-iodo amides.

13 Claims, No Drawings

(56) References Cited

OTHER PUBLICATIONS

Cristol et al.; "Convenient synthesis of alkyl halides from carboxylic acids" J. Org. Chem. 26:280, (1961).
Cvengros; "A Concise Synthesis of ortho-Iodobenzyl Alcohols via Addition of ortho-Iodophenyl Grignard Reagent to Aldehydes and Ketones" Synthesis (16): 2818-2824, (2009).
Dmitrii et al.; "An improved protocol for ligandless SuzukiMiyaura coupling in water" Tetrahedron Letters vol. 47, Issue 25, pp. 4225-4229. Jun. 19, 2006.
e-EROS Encyclopedia of Reagents for Organic Synthesis, (2010).
Griffiths et al.; "Thermochemical properties of iodinated cubane derivatives" Thermochimica Acta vol. 499, Issues 1-2, pp. 15-20, Feb. 20, 2010.
Johnson et al.; "The Degradation of Carboxylic Acid Salts by Means of Halogen—The Hunsdiecker Reaction" Chem. Rev. 56 (2), pp. 219-269, (1956).
Kaiser et al.; "Synthesis and aromatisation of cyclic enediyne-containing amino acids" Org. Biomol. Chem. 7, 695-705, (2009).
Kulbitski et al.; "Metal-Free Efficient, General and Facile Iododecarboxylation Method with Biodegradable Co-Products" Adv. Synth. Catal. 353, 1438-1442, (2011).
Menche et al.; "Design, synthesis, and biological evaluation of novel analogues of archazolid: a highly potent simplified V-ATPase inhibitor" Bioorg Med Chem Lett. ;17(6):1732-5, Mar. 15, 2007.
Naskar; "Catalytic Hunsdiecker Reaction and One-Pot Catalytic Hunsdiecker-Heck Strategy: Synthesis of alpha,beta- Unsaturated Aromatic Halides, alpha-(Dihalomethyl)benzenemethanols, 5-Aryl-2,4-pentadienoic acids, Dienoates and Dienamides", Tetrahdron,vol. 56, pp. 1369-1377, (2000).
Naskar; "1-Haloalkynes from propiolic acids: a novel catalytic halodecarboxylation protocol" J. Org. Chem. 64, pp. 6896-6897, (1999).
Naskar et al.; "Is Metal Necessary in the Hunsdiecker-Borodin Reaction" Tetrahedron Letters 39, 699-702, (1998).
Pasternak et al.; Potent heteroarylpiperidine and carboxyphenylpiperidine 1-alkyl-cyclopentane carboxamide CCR2 antagonists. Bioorg Med Chem Lett. 18(3):994-8. Feb. 1, 2008.
Prakash et al.; "Catalytic Hunsdiecker Reaction of α,β-Unsaturated Carboxylic Acids: How Efficient Is the Catalyst?" J. Org. Chem. 67, 7861-7864. (2002).
Rajanna et al.; "Micellar Mediated Halodecarboxylation of α,β-Unsaturated Aliphatic and Aromatic Carboxylic Acids—a Novel Green Hunsdiecker—Borodin Reaction" Journal of Dispersion Science and Technology, 28:613-616, (2007).
Rodrigo et al.; "Triiodoisocyanuric acid: a new and convenient reagent for regioselective coiodination of alkenes and enolethers with oxygenated nucleophiles" Tetrahedron Letters vol. 48, Issue 49, pp. 8747-8751, Dec. 3, 2007.
Sheldon et al.; "Oxidative Decarboxylation of Carboxylic Acids by Lead Tetraacetate" Org. React. (N.Y.), 19, 279, (1972).
Silbert; "Reactions of Peroxides: II. Reaction of Carboxylic Acids With Iodine and Peroxides" J Am Oil Chem ;46:615, (1969).
Sivakumar; "Direct radical substitution on the cubane skeleton" Tetrahedron Letters vol. 31, Issue 6, pp. 805-806, (1990).
Still et al.; "Rapid chromatographic technique for preparative separations with moderate resolution" J. Org. Chem, 43 (14), pp. 2923-2925, (1978).
Suarez et al.; "Photoinduced conversion of hydroxyl-containing substrates with hypervalent iodine I (III) I2 to the corresponding oxygen-centered radical". Tetrahedron J. Org. Chem. 51, 402 (1986).
Trost et al.; "Comprehensive Organic Synthesis" 7, pp. 717. (1991).
Vitold et al.; "2,4,6,8-Tetraiodoglycoluril in sulfuric acid as a new powerful reagent for iodination of deactivated arenes" Tetrahedron Letters vol. 41, Issue 47, pp. 9101-9104, Nov. 18, 2000.
Villalobos et al.; "5,7-dihydro-3-[2-[1-(phenylmethyl)-4-piperidinyl]ethyl]-6H-pyrrolo[3,2-f]-1,2-benzisoxazol-6-one: a potent and centrally-selective inhibitor of acetylcholinesterase with an improved margin of safety" J Med Chem. 38(15)2802-8. Jul, 21, 1995.
Barnes R. A. et. al., "The Reaction of Bromine with Silver Salts of Aromatic Acids", J. Am. Chem. Soc., 1950, v. 72, 3188-3191.
Bovonsombat P. et. al., Regioselective iodination of phenol and analogues using N-iodosuccinimide and p-toluenesulfonic acid, Tetrahedron Lett. 2009, v. 50, 2664-2667.
Carreno M. C. et. al., 'Mild and regiospecific nuclear iodination of methoxybenzenes and naphthalenes with N-iodosuccinimide in acetonitrile', Tetrahedron Lett. 1996, v. 37, 4081-4084.
Chaikovskii V. K. et. al., 'Synthesis of N-Iodosuccinimide and Its Application in H2SO4 as Efficient Iodination Reagent for Deactivated Aromatic Compounds', Russ. J. Org. Chem. 2001, v. 37, 1503-1504.
Chaikovskii V. K. et. al., 'Superactivity and dual reactivity of the system N-iodosuccinimide-H2SO4 in the iodination of deactivated arenes', Russ. J. Org. Chem. 2007, v. 43, 1278-1281.
Chaikovskii V. K. et. al., '1,3-Diiodo-5,5-dimethylhydantoin—An efficient reagent for iodination of aromatic compounds', Russ. J. Org. Chem. 2007, v. 43, 1291-1296.
Chaykovskiy, V. K. et. al., "Investigation of Preparative Possibilities of Iodinating Systems on the Basis of N-Iodoacetamide", Bulletin of the Tomsk Polytechnic University, 2007, v. 311(3):88-90.
Dolenc D., 'N-Iodosaccharin—a New Reagent for Iodination of Alkenes and Activated Aromatics', Synlett 2000(4): 544-546.
Fotsch C. et. al., 'Further studies with the 2-amino-1,3-thiazol-4(5H)-one class of 11beta-hydroxysteroid dehydrogenase type 1 inhibitors: reducing pregnane X receptor activity and exploring activity in a monkey pharmacodynamic model', J. Med. Chem. 2008, v. 51, 7953-7967.
Fursule R. A. et. al., 'Novel system for decarboxylative bromination of alpha,beta-unsaturated carboxylic acids with diacetoxyiodobenzene', Chem. Pharm. Bull. 2009, v. 57, 1243-1245.
Hamdouchi C. et. al., '2-Amino-3-substituted-6-[(E)-1-phenyl-2-(N-methylcarbamoyl)vinyl]imid azo[1,2-a]pyridines as a novel class of inhibitors of human rhinovirus: stereospecific synthesis and antiviral activity', J. Med. Chem. 1999, v. 42, 50-59.
Hamdouchi C. et. al., 'Imidazo[1,2-b]pyridazines, novel nucleus with potent and broad spectrum activity against human picornaviruses: design, synthesis, and biological evaluation', J. Med. Chem. 2003, v. 46, 4333-4341.
Huang Y-L. et. al., 'Concise bromodecarboxylation of cinnamic acids to β-bromostyrenes', Tetrahedron Lett. 2009, v. 50, 1834-1837.
Kanury V. S. et. al., 'Photochemical transformations—V a: Organic iodides (part 4) : solution photochemistry of 4-phenyl-l-iodobotane and 4-phenyl-l-bromobutane', Tetrahedron 1987, v. 43, 2543-2548.
Kemp K. C. et. al., 'Neighboring-group and substituent effects in the solvolysis of substituted .alpha.-bromophenylacetate ions', J. Org. Chem. 1968, v. 33, 4165-4168.
Kuang, C. et. al. "Stereoselective Synthesis of (E)-b-Arylvinyl Halides by Microwave-Induced Hunsdiecker Reaction", Synlett, 2000, v. 10, 1439-1442.
Lecat-Guillet N. et. al., 'Synthesis and Evaluation of Imidazo[2,1-b]thiazoles as Iodide Efflux Inhibitors in Thyrocytes', ChemMedChem 2009, v. 4, 1819-1830.
Olah G. A. et. al., 'Synthetic methods and reactions. 181. Iodination of deactivated aromatics with N-iodosuccinimide in trifluoromethanesulfonic acid (NIS-CF3SO3H) via in situ generated superelectrophilic iodine(I) trifluoromethanesulfonate', J. Org. Chem. 1993, v. 58, 3194-3195.
Olimpieri F. et. al., 'Regioselective multicomponent sequential synthesis of hydantoins', Org. Biomol. Chem. 2012, v. 10, 9538-9555.
Orazi O. O. et. al., 'n-iodohydantoins. II. Iodinations with 1,3-diiodo-5,5-dimethylhydantoin', J. Org. Chem. 1965, v. 30, 1101-1104.
Panaiotov, I. M., "Reactions of N-bromosuccinimide with some arylacetic acids", Abstract, Izvest. Khim. Inst. Bulgar Akad. Nauk, v. 5, 183-92, 1957.
Panaiotov, I. M., "On the Reaction Between N-Bromosuccin'mide and Certain Arylacetic Acids", Doklady Bolgarskoi Akademii Nauk,v. 10(2): 137-40, 1957.
Pospisil J. et. al., 'Total Synthesis of the Aspercyclides', Chem. Eur. J. (2009), vol. 15, pp. 5956-5968.
Prakash G. K. et. al., 'N-halosuccinimide/BF3-H2O, efficient electrophilic halogenating systems for aromatics', J. Am. Chem. Soc., 2004, v. 126, 15770-6.

(56) References Cited

OTHER PUBLICATIONS

Rodrigo Da S. R. et. al., 'Triiodoisocyanuric acid: a new and convenient reagent for regioselective iodination of activated arenes', J. Braz. Chem. Soc. 2008, v. 19, 1239-1243.
Sabbatini F. M. et. al., 'Discovery process and characterization of novel carbohydrazide derivatives as potent and selective GHSR1a antagonists', ChemMedChem 2010, v. 5, 1450-1455.
Tanemura K. et. al., 'Halogenation of Aromatic Compounds by N-chloro-, N-bromo-, and N-iodosuccinimide', Chem. Lett. 2003, v. 32, 932-933.
Telvekar V. N. et. al., 'A novel system for decarboxylative bromination', Tetrahedron Lett. 2007, v. 48, 4529-4532.
Telvekar V. N. et. al., 'A novel method for bromodecarboxylation of α,β-unsaturated carboxylic acids using catalytic sodium nitrite', Tetrahedron Lett. 2011, v. 52, 2394-2396.
Wang P. et. al., 'Preparation of isotopically labelled benzophenone-containing lipid analogues', J. Label. Compd. Radiopharm. 2005, v. 48, 781-788.
Wilson, C. V., "Organic Reactions: The Reaction of Halogens With Silver Salts of Carboxylic Acids", 1957, John Wiley & Sons, Inc, London, V. IX, Chapter 5, pp. 333-374.
Yadav J. S. et. al., 'Efficient Halogenation of Aromatic Systems Using N-Halosuccinimides in Ionic Liquids', Adv. Synth.Catal. (2004), vol. 346, pp. 77-82.
Zhang L. H. et. al., 'A simple and efficient method of preparing α-bromo carboxylic acids', Tetrahedron Lett. 1998, v. 39, 9621-9622.
Zhang, Y. et. al., 'Lewis Acid Catalyzed Highly Selective Halogenation of Aromatic Compounds', Synlett 2005(18): 2837-2842.
Chaikovski et al.; "Iodination of aromatic compounds by N-iodosuccinimide in organic solvents in the presence of H2SO4", lzvestiya Vysshikh Uchebnykh Zavedenii, Khimiya i Khimicheskaya Tekhnologiya, vol. 45, Issue: 3, pp. 48-51 Journal, 2002.
Crombie et al.; "Ring Expansion-Annulation Strategy for the Synthesis of Substituted Azulenes and Oligoazulenes. 2. Synthesis of Azulenyl Halides, Sulfonates, and Azulenylmetal Compounds and Their Application in Transition-Metal-Mediated Coupling Reactions", J. Org. Chem. 2004, 69, 8652.
Huang et al.; "The Relative Stabilising Influences of Substituents on Free Alkyl Radicals. Part V. Selective Bromination by N-Bromosuccinimide", J. Chem. Soc., 1958, 2637-2640.
MacDonald et al.; "Nucleophilic substitution of alkyl iodides via oxidative ligand transfer", *J. Org. Chem.*, 1985, 50 (24), pp. 5000-5001, Nov. 1985.
McGarvey et al.; "An Introductory Level Kinetics Investigation", *J. Chem. Educ.*, 1980, 57 (2), p. 155.
Nascar et al.; "Novel Catalytic Hunsdiecker—Heck (CHH) Strategy toward All-E Stereocontrolled Ferrocene-Capped Conjugated Push-Pull Polyenes", *Organometallics*, 2000, 19 (8), pp. 1464-1469.
Roderick et al.; "The Reaction of Bromine with Silver Salts of Aromatic Acids", JACS vol. 72, 1950, pp. 3188-3190.
Tan et al.; "A Polar Effects Controlled Enantioselective 1,2-Chlorine Atom Migration via a Chlorine-Bridged Radical Intermediate", J. Am. Chem. Soc., 2002, 124 (10), pp. 2078-2079.

* cited by examiner

US 8,822,516 B2

PROCESS FOR THE PREPARATION OF IODIDES

CROSS-REFERENCE TO RELATED APPLICATIONS

This application is a National Phase Application of PCT International Application No. PCT/IL2011/000458, entitled "PROCESS FOR THE PREPARATION OF IODIDES", International Filing Date Jun. 9, 2011, published on Dec. 15, 2011 as International Publication No. WO 2011/154953, which in turn claims priority from U.S. Provisional Patent Application No. 61/353,427, filed Jun. 10, 2010 and U.S. Provisional Patent Application No. 61/427,925, filed Dec. 29, 2010, all of which are incorporated herein by reference in their entirety.

FIELD OF THE INVENTION

This invention is directed to a process for the preparation of high yield alkyl or aryl iodide from its corresponding carboxylic acid using N-iodo amides.

BACKGROUND OF THE INVENTION

The rich chemistry of the carbon-iodine bond has made it a particularly rewarding synthetic tool of routine use for the purpose of functional group interconversion. Organic iodides are valuable and versatile intermediates in the synthesis of functional materials and biologically active compounds such as medical drugs and agricultural chemicals. In particular, alkyl and aryl iodides serve as excellent substrates for transition metal-catalyzed homo- and cross-coupling reactions, which are used for the synthesis of complex molecules. As the iodine atom is an excellent leaving group, iodosubstituted organic compounds have been recognized as valuable synthons or precursors in organic synthesis, above all in carbon-carbon, carbon-nitrogen, carbon-oxygen or carbon-sulfur bond formation.

Thus, various organic iodides have been produced commercially and have been used in laboratory and industrial synthesis. For example, 1-Boc-4-iodomethylpiperidine is the starting material for the synthesis of donepezil and icopezil and 1-Boc-4-iodopiperidine is used for the synthesis of 4-arylpiperidine moiety, which is a structural feature which can be found in a wide variety of active pharmacologic agents. The iodides also find use as intermediates in the preparation of other compounds, especially zinc organic compounds. Nucleophilic displacement reactions of the iodides yield sulfonic acid esters, nitro derivatives and mercaptans.

Aromatic iodides possess a much higher reactivity than other aromatic halides in Ullmann condensation reactions. Typically, aryl iodides have higher kinetic rates of product formation than other aromatic halides, as illustrated by the reduced reaction times necessary to produce higher yields of highly pure products than with other aromatic halides. Thus, aryl iodides are key substrates in the Ullmann condensation reactions traditionally used to manufacture charge transporting and hole transporting triarylamine compounds (U.S. Pat. No. 7,138,555).

Nucleophilic iodination of organic hydroxy, chloro, and bromo derivatives is usually used for the formation of organic iodides. For example, 1-Boc-4-iodopiperidine and 1-Boc-4-iodomethylpiperidine were prepared from related hydroxy-derivatives by reaction with iodine and triphenylphosphine. The disadvantages of such reactions include difficulties in separation and utilization of triphenylphosphine oxide as main by-product of the reactions.

Carboxylic acids are widely available and cheap raw materials in the organic synthesis, so the oxidative decarboxylation of carboxylic acids with concomitant replacement by iodine (iodo-de-carboxylation) comprises an extremely useful procedure for the syntheses of organic iodides. The unreacted acid may be easily recovered by treatment of the iodo-de-carboxylation reaction mixture with aqueous base and then acid. This makes the reaction also attractive for iodo-de-carboxylation of acids with low reactivity.

The Hunsdiecker reaction (Johnson, *Chem. Rev.* 1956, v. 56, 219) includes an iodo-de-carboxylation reaction, by treatment of anhydrous silver salt of the acid with iodine in an inert solvent. However, the reaction is extremely sensitive to trace amounts of water, the presence of which leads to the recovery of unreacted acid. Unfortunately, the preparation of dry silver salts of carboxylic acids is difficult and, such salts are usually quite sensitive to heat also, they are often quite hard to dry thoroughly. Another way to perform the Hunsdiecker reaction is by use of a mixture of the acid and $I_2$/HgO (Cristol & Firth, *J. Org. Chem.* 1961, v. 26, 280) or $I_2$/Pb(OAc)$_4$ (Barton et al., *J. Chem. Soc.*, 1965, 2438) instead of the silver salt. Accordingly, the Hunsdiecker reaction and/or its modifications use heavy metal salts such as those of silver, mercury and lead and the disadvantages of such procedures for pharmaceutical industry are obvious.

The Barton iodo-de-carboxylation procedure (Barton et al., Tetrahedron 1985, v. 41, 3901 and *Tetrahedron,* 1987, v. 43, 4321) includes conversion of carboxylic acids to the esters of N-hydroxypyridine-2-thione. The thiohydroxamic esters are iodinated by $CHI_3$, and $CH_2I_2$ in cyclohexene solution. Thiopyridines are formed in the reaction as significant by-products.

Another method for the conversion of R—COOH to R—I includes reacting carboxylic acids with iodine and dibenzoyl peroxide. High concentration of peroxide in the reaction mixture may promote explosive. Iodobenzene is formed in the reaction as a significant by-product.

Additional process for converting carboxylic acids to their corresponding iodides is by treating the carboxylic acid with (diacetoxyiodo)benzene (DIB) and iodine under irradiation conditions (Suarez et al., *J. Org. Chem.* 1986, v. 51, 402 and Boto et al., *Eur. J. Org. Chem.* 2005, 673); wherein iodobenzene was formed in the reaction as significant by-product.

Barton used tert-butyl hypoiodite in a Hunsdieker type reaction to iodo-decarboxylate carboxylic acids. tert-Butyl hypoiodite is not commercially available reagent, has low thermal stability of the reagent and should be used immediately after preparation. Therefore, tert-butyl hypoiodite cannot be used for the preparation of aryl-iodide compounds.

N-iodo amides such as N-iodosuccinimide (NIS), N-iodosaccharine (NISac), 1,3-diiodo-5,5-dimethylhydantoin (DIH), triiodoisocyanuric acid (TICA) (*Tetrahedron Letters* 2007, v. 48, 8747), 2,4,6,8-tetraiodoglycoluril (TIG) (*Tetrahedron Letters* 2000, v. 41, 9101) etc., are used as efficient reagents for the electrophilic iodination of organic compounds.

NIS   DIH   TIG

NISac   TICA

However, the use of these reagents as source of iodine for reactions of iodo-de-carboxylation are limited. Reaction of N-halosuccinimides with aryl acrylic and aryl propiolic acids gives 1-halo-2-aryl-1-alkenes and 1-halo-2-aryl-1-alkynes (*J. Org. Chem.* 2002, v. 67, 7861; *J. Org. Chem.* 1999, v. 64, 6896; *J. Org. Chem.* 1997, v. 62, 199; *Tetrahedron* 2000, v. 56, 1369). All the reactions occur in the presence of catalyst. Reaction of α-(cyclopropylsulfonyl)phenylacetic acid with NIS gives α-iodobenzyl cyclopropyl sulfone only with 32% yield (*J. Org. Chem.* 1974, v. 39, 2516).

SUMMARY OF THE INVENTION

In one embodiment, this invention is directed to a process for the preparation of iodide, represented by scheme (1):

R—COOH→R—I    (1)

comprising reacting R—COOH with N-iodo amide to yield R—I; wherein R is saturated, linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to an iodinated compound represented by formula R—I, prepared according to the process of claim 1; wherein said R is saturated, linear or branched, substituted or unsubstituted alkyl; substituted or unsubstituted aryl; saturated or unsaturated, substituted or unsubstituted mono- or poly-carbocyclic or heterocyclic ring.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to a process for the preparation of iodide R—I, represented by scheme (1):

R—COOH→R—I    (1)

comprising reacting R—COOH with an iodinating agent to yield R—I;

wherein R is saturated or unsaturated, linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising reacting R—COOH with a N-iodo amide to yield R—I; wherein R is saturated or unsaturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising reacting R—COOH with a N-iodo amide to yield R—I; wherein R is saturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising reacting R—COOH with a N-iodo reagent, wherein said reagent includes any N-iodo organic compound or a mixture of one or more N-iodo organic compounds; wherein R is saturated or unsaturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising reacting R—COOH with mono or poly N-iodo hydantoins, N-iodo succinimide, N-iodo saccharine, mono or poly N-iodo isocyanuric acid, mono or poly N-iodo glycoluril, or mixture thereof to yield R—I; wherein R is saturated or unsaturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising reacting R—COOH with 1,3-diiodo-5,5-dimethylhydantoin (DIH), N-iodosuccinimide (NIS), triiodoisocyanuric acid (TICA), 2,4,6,8-tetraiodoglycoluril (TIG), N-iodosaccharine (NISac), 1-iodo-5,5-dimethylhydantoin, 3-iodo-5,5-dimethylhydantoin or mixture thereof to yield R—I.

In one embodiment, this invention is directed to a process for the preparation of iodide, represented by scheme (1):

R—COOH→R—I    (1)

comprising reacting R—COOH with 1,3-diiodo-5,5-dimethylhydantoin (DIH), 1-iodo-5,5-dimethylhydantoin, 3-iodo-5,5-dimethylhydantoin or mixture thereof to yield R—I; wherein R is saturated or unsaturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

R—COOH→R—I    (1)

comprising formation of carbon-centered radical R, derived formally by removal of carboxyl group from R—COOH, in reaction of R—COOH with a N-iodo amide and following reaction of the free radical R. with N-iodo amide to yield R—I; wherein R is saturated or unsaturated linear or branched, substituted or unsubstituted alkyl; substituted or unsubstituted aryl; saturated or unsaturated, substituted or unsubstituted mono- or poly-carbocyclic or heterocyclic ring.

In one embodiment, this invention is directed to a process for the preparation of iodide, represented by scheme (1):

(1)

comprising reacting R—COOH with N-iodo reagent to yield R—I; wherein the yield of the reaction is between 80-100%; wherein R is saturated or unsaturated, linear or branched, substituted or unsubstituted alkyl; substituted or unsubstituted aryl; saturated or unsaturated, substituted or unsubstituted mono- or poly-carbocyclic or heterocyclic ring.

In one embodiment, N-iodo reagent of this invention is used in the iodo-de-carboxylation reaction (1). In another embodiment the N-iodo reagent of this invention is a N-iodo organic compound. In another embodiment, the N-iodo organic compound is a compound which possess a chemically bonded iodine and nitrogen atoms (nitrogen-iodo or "N—I").

In one embodiment, the N-iodo reagent or N-iodo organic compound is N-iodo amide compound. In another embodiment, the N-iodo amide is a primary amide. In another embodiment, the N-iodo amide is a secondary amide. In another embodiment, the amide is carboxamide, sulfonamide, lactame, carbamate, imide or ureide or combination thereof. In another embodiment the amide is 5,5-dimethylhydantoin, 3-benzyl-5,5-dimethylhydantoin, 5-methyl-5-phenylhydantoin, 5,5-diphenylhydantoin, 5,5-hexamethylenehydantoin, 5,5-pentamethylenehydantoin, 5,5-tetramethylenehydantoin, succinimide, phthalimide, saccharine, isocyanuric acid, 5,5-dimethylbarbituric acid, glycoluril, 3a,6a-diphenylglycoluril, 3a,6a-dimethylglycoluril, 4,4,5,5-tetramethyl-2-imidazolidinone, 4,4-dimethyl-2-oxazolidinone or combination thereof.

In one embodiment, the N-iodo amide is a primary amide. In another embodiment, the primary amide is carboxamide. In another embodiment, the carboxamide is RC(=O)NHR such as lactone or a peptide. In another embodiment, the carboxamide is RNHC(=O)OR (carbamate) such as t-BuNHBoc, derivatives of 2-ixazolidinone (4,4-dimethyl-2-oxazolidinone). In another embodiment, the carboxamide is RNHC(=O)NHR (derivative of urea) such as derivatives of 2-imidazolidinone (4,4,5,5-tetramethyl-2-imidazolidinone), glycoluril and its derivatives (3a,6a-diphenylglycoluril, 3a,6a-dimethylglycoluril).

In one embodiment embodiment, the N-iodo amide is a primary amide, wherein said primary amide is sulfonamide. In another embodiment, the sulfonamide is RS(=O)$_2$NHR or RNHS(=O)$_2$NHR.

In one embodiment embodiment, the N-iodo amide is a primary amide, wherein said primary amide is phosphoramide. In another embodiment, the phosphoramide is R$_2$P(=O)NHR.

In one embodiment embodiment, the N-iodo amide is a primary amide, wherein said primary amide is nitramide. In another embodiment, the nitramide is O$_2$NNHR.

In one embodiment embodiment, the N-iodo amide is a secondary amide. In another embodiment, the secondary amide is an imide [RC(=O)]$_2$NH. In another embodiment the imide is succinimide or phthalimide.

In another embodiment, the N-iodo amide is a secondary amide. In another embodiment, the amide is RS(=O)$_2$NHC(=O)R, RS(=O)$_2$NHS(=O)$_2$R, RHNC(=O)NHC(=O)R, RC(=O)NHC(=O)NHC(=O)R, RS(=O)$_2$NHC(=O)NHC(=O)R, or RS(=O)$_2$NHC(=O)NHS(=O)$_2$R (ureides). Non limiting examples of ureides include derivatives of hydantoin (5,5-dimethylhydantoin, 3-benzyl-5,5-dimethylhydantoin, 5-methyl-5-phenylhydantoin, 5,5-diphenylhydantoin, 5,5-pentamethylenehydantoin, 5,5-hexamethylenehydantoin, 5,5-tetramethylenehydantoin); isocyanuric acid; and derivatives of barbituric acid (5,5-diethylbarbituric acid, 5,5-dimethylbarbituric acid or 5-ethyl-5-isoamylbarbituric acid).

In another embodiment, the amide is sulfonamide. In another embodiment, the amide is lactame. In another embodiment, the amide is carbamate. In another embodiment, the amide is imide. In another embodiment, the amide is ureide. In another embodiment, the amide is 5-dimethylhydantoin. In another embodiment, the amide is 3-benzyl-5,5-dimethylhydantoin. In another embodiment, the amide is 5-methyl-5-phenylhydantoin. In another embodiment, the amide is 5,5-diphenylhydantoin. In another embodiment, the amide is 5,5-hexamethylenehydantoin. In another embodiment, the amide is 5,5-pentamethylenehydantoin. In another embodiment, the amide is 5,5-tetramethylenehydantoin. In another embodiment, the amide is succinimide. In another embodiment, the amide is phthalimide. In another embodiment, the amide is saccharine. In another embodiment, the amide is isocyanuric acid. In another embodiment, the amide is 5,5-dimethylbarbituric acid. In another embodiment, the amide is glycoluril. In another embodiment, the amide is 3a,6a-diphenylglycoluril. In another embodiment, the amide is 3a,6a-dimethylglycoluril. In another embodiment, the amide is 4,4,5,5-tetramethyl-2-imidazolidinone. In another embodiment, the amide is 4,4-dimethyl-2-oxazolidinone.

In another embodiment, the N-iodo amide is mono or poly iodinated hydantoins, mono or poly iodinated succinimide, mono or poly iodinated saccharine, iodinated cyanuric acid, iodinated glycoluril, or mixture thereof. In another embodiment, the N-iodo amide is mono or poly iodinated hydantoins. In another embodiment, the N-iodo amide is mono or poly iodinated succinimide. In another embodiment, the N-iodo amide is mono or poly iodinated saccharine. In another embodiment, the N-iodo amide is iodinated mono or poly cyanuric acid. In another embodiment, the N-iodo amide is cyanuric acid iodinated glycoluril.

In another embodiment, the N-iodo amide is 1,3-diiodo-5,5-dimethylhydantoin (DIH), N-iodosuccinimide (NIS), triiodoisocyanuric acid (TICA), 2,4,6,8-tetraiodoglycoluril (TIG), N-iodosaccharine (NISac), 1-iodo-5,5-dimethylhydantoin, 3-iodo-5,5-dimethylhydantoin or mixture thereof. In another embodiment, the N-iodinated reagent is 1,3-diiodo-5,5-dimethylhydantoin (DIH). In another embodiment, the N-iodinated reagent is N-iodosuccinimide (NIS). In another embodiment, the N-iodinated reagent is triiodoisocyanuric acid (TICA). In another embodiment, the N-iodinated reagent is 2,4,6,8-tetraiodoglycoluril (TIG). In another embodiment, the N-iodinated reagent is N-iodosaccharine (NISac). In another embodiment, the N-iodinated reagent is 1-iodo-5,5-dimethylhydantoin. In another embodiment, the N-iodinated reagent is 3-iodo-5,5-dimethylhydantoin.

Non limited examples of N-iodinated reagent is selected from N-iodocarboxamides represented by formula (2):

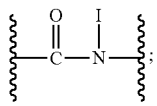

N-iodosulfonamides represented by formula (3):

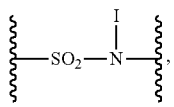

In another embodiment, the process of this invention does not include a catalyst. In another embodiment the iodo-de-carboxylation process of this invention includes a photocatalyst. In another embodiment, the process of this invention is a radical reaction.

In one embodiment, the N-iodo reagent ("N—I") is being used freshly after its preparation. In another embodiment, the N-iodo reagent is prepared immediately before the desired iodo-de-carboxylation reaction. In another embodiment, the N-iodo reagent is prepared in the same reaction pot of the iodo-de-carboxylation reaction (1) (one-pot reaction) or formed in situ in the reaction mixture of the iodo-de-carboxylation reaction (1). In another embodiment, DIH, NIS and NISac are commercially available and are stable, therefore can be prepared prior to the iodo-de-carboxylation reaction (1).

1,3-Diiodo-5,5-dimethylhydantoin (DIH) is a stable commercially available reagent, and is obtained in high yield by the reaction of an alkaline aqueous solution of 5,5-dimethylhydantoin with iodine monochloride.

In one embodiment, this invention is directed to iodo-de-carboxylation of R—COOH to yield R—I. In another embodiment R is a saturated alkyl. In another embodiment R is an unsaturated alkyl. In another embodiment R is a substituted saturated alkyl. In another embodiment R is a substituted unsaturated alkyl. In another embodiment R is a linear substituted or unsubstituted saturated alkyl. In another embodiment R is a linear substituted or unsubstituted unsaturated alkyl. In another embodiment R is a branched substituted or unsubstituted saturated alkyl. In another embodiment R is a branched substituted or unsubstituted unsaturated alkyl. In another embodiment R is substituted or unsubstituted aryl. In another embodiment R is substituted or unsubstituted phenyl. In another embodiment R is substituted or unsubstituted naphthyl. In another embodiment R is saturated or unsaturated, substituted or unsubstituted mono- or poly-carbocyclic. In another embodiment R is saturated or unsaturated, substituted or unsubstituted mono- or poly heterocyclic ring.

In one embodiment, if the R group of R—COOH possess an additional functional group such as hydroxyl, amine, aldehyde, thio, or combination thereof, such functional group is protected. In another embodiment, R—COOH is N-protected 4-piperidinecarboxylic acid, N-protected 4-piperidineacetic acid, N-protected azetidine-3-carboxylic acid, mono-alkyl phthalate, iodobenzoic acid, bromobenzoic acid or biphenyl-4-carboxylic acid.

In one embodiment R—COOH is not ECH(R)COOH, where E is acyl, $SR_2^+$, or $NR_3^+$ and R is either an hydrogen, alkyl or an aryl.

In one embodiment, substituted R of R—I is a protected functional groups, such as protected hydroxyl, protected thio and/or protected amino groups which can further be removed by methods known in the art to obtain the free thio, free hydroxyl and/or free amino groups respectively.

In one embodiment, this invention provides a process for the preparation of N-protected 3-iodoazetidine (R—I) from N-protected azetidine-3-carboxylic acid (R—COOH).

In one embodiment, this invention provides a process for the preparation of N-protected 4-(iodomethyl)piperidine (R—I) from N-protected 4-piperidineacetic (R—COOH).

In one embodiment, this invention provides a process for the preparation of 2-iodobenzoate (R—I) from mono-alkyl phthalate (R—COOH).

In one embodiment, this invention provides a process for the preparation of o-diiodobenzene (R—I) from 2-iodobenzoic acid (R—COOH).

In one embodiment, this invention provides a process for the preparation of 4-iodobiphenyl (R—I) from biphenyl-4-carboxylic acid (R—COOH).

In one embodiment, the process of this invention is conducted in the presence of a solvent. In another embodiment, the solvent is an organic solvent. In another embodiment, the solvent is a hydrocarbon. In another embodiment, the solvent is halocarbon. In another embodiment, the solvent is an ester. Non limiting examples of esters are ethyl acetate or butyl acetate. In another embodiment, the solvent is nitromethane. In another embodiment, the solvent is acetonitrile. In another embodiment, the solvent is hydrocarbon, halocarbon, acetonitrile or any combination thereof. In another embodiment, the solvent is hydrocarbon solvent, halocarbon solvent, ester, acetonitrile, nitromethane or any combination thereof. In another embodiment, the reaction between R—COOH and the iodinating reagent is in the presence of a solvent.

The term "hydrocarbon solvent" refers to any solvent consisting of the carbon and hydrogen elements. Non limiting examples of hydrocarbon solvents are cyclohexane, cyclopentane, heptane, pentane hexane, or benzene.

The term "halocarbon solvent" refers to any solvent wherein one or more of the carbons are covalently linked to one or more halogens (fluorine, chlorine, bromine or iodine). Non limiting examples of halocarbon solvents are chloroform, dichloromethane, chlorobenzene, 1,2-dichloroethane, carbon tetrachloride, 1,3-dichloropropane, 1,1,2,2-tetrachlorodifluoroethane, 1,1,2-trichloroethane, trichloroethylene, perchloroethylene, bromobenzene 1,1,2-trichlorotrifluoroethane or 1,2-dibromoethane.

In one embodiment, R—I is purified from the reaction mixture by washing, chromatography, crystallization or any combination thereof. In another embodiment R—I is purified from the reaction mixture by a washing step. In another embodiment the washing step comprises washing with an aqueous reducing agent followed by washing with an aqueous base. In another embodiment the washing step comprises washing with an aqueous base followed by washing with an aqueous reducing agent. In another embodiment, the washing step comprises washing with an aqueous reducing agent and a base.

In another embodiment, the washing step comprises washing of the reaction mixture with aqueous reducing agent, wherein excess of the "N—I" iodinated reagent is converted to water-soluble N—H compounds, and thereby removed from the organic phase. For example, DIH and 1-iodo-5,5-dimethylhydantoin and 3-iodo-5,5-dimethylhydantoin side products are converted to water-soluble 5,5-dimethylhydantoin. In another embodiment, an aqueous reducing agent refers to an aqueous solution comprising a reducing agent. Non limiting examples of reducing agents are $Na_2SO_3$, $NaHSO_3$, $Na_2S_2O_3$, $NaBH_4/NaOH$ or combination thereof. In another embodiment the reducing agent is added at a concentration of between 1-10% w/w to the water to obtain an aqueous reducing agent solution.

In one embodiment, the process of this invention directed to iodo-de-carboxylation (1) comprising a washing step with an aqueous reducing agent. In another embodiment, following the washing step a potassium iodide starch paper test is performed to identify traces of the N-iodo reagent. "A potassium iodide starch paper test" (SPT) refers to a starch iodide test paper that has been wetted with aqueous acetic acid; 1/1; v/v]. In another embodiment, if the test is positive, an additional aqueous reducing agent is added to the reaction mixture.

In another embodiment, the washing step comprises washing the reaction mixture with an aqueous base, wherein the unreacted carboxylic acid is removed from the organic phase by washing with an aqueous base. In another embodiment, the carboxylic acid is recovered by acidifying the aqueous phase. In another embodiment, an aqueous base refers to an aqueous solution comprising a base. Non limiting examples of a base is $NaHCO_3$, $NaOH$, $Na_2CO_3$, $KOH$, $Na_2SO_3$ or combination thereof.

In another embodiment the base is added at a concentration of between 1-10% w/w to the water to obtain an aqueous base solution.

In another embodiment, the washing step of an aqueous reducing agent is conducted before the washing step of the aqueous base. In another embodiment, the washing step of the aqueous base is conducted before the washing step of the aqueous reducing agent. In another embodiment, the washing step comprises washing with an aqueous reducing agent and a base. Such a combination of an aqueous reducing agent and a base includes $Na_2SO_3$ and $NaBH_4/NaOH$ which are basic reducing agents that combine properties of reducing agent and a base.

In another embodiment, the washing steps of this invention are conducted using the organic solvent of the reaction mixture as the organic phase. In another embodiment, the washing step of the aqueous base and the washing step of the aqueous reducing agent are independently performed using a) the organic solvent of the reaction mixture, b) a mixture of organic solvents, or c) a different organic solvent, as the organic phase. Non limiting examples of organic solvents used as an organic phase in the washing step are hydrocarbon solvent, halocarbon solvent, or esters such as cyclohexane, heptane, hexane, pentane, benzene, toluene, chlorobenzene, 1,2-dichloroethane, carbon tetrachloride, 1,3-dichloropropane, 1,1,2,2-tertrachlorodifluoroethane, 1,1,2-trichloroethane, trichloroethylene, perchloroethylene, dichloromethane, chloroform, ethyl acetate or butyl acetate.

In one embodiment, following the washing step, the aqueous phase is treated with an acid or an aqueous acid solution and extracted by organic solvent to isolate starting carboxylic acid. Alternatively, the acidified aqueous phase is cooled to 0-5° C. to precipitate solid starting carboxylic acid.

In one embodiment, the organic iodine product is soluble in organic phase and not soluble in the aqueous phase. In another embodiment, the crude organic iodide is isolated from reaction mixture by standard organic solvent extractive work-up.

In one embodiment, removing the solvent from the organic phase give crude desired iodide (R—I) as the residue. In another embodiment, the residue is pure desired iodide (R—I). In another embodiment, the iodide is purified by crystallization, rectification or chromatography of the residue.

In one embodiment, the process of this invention provides a process for the preparation of pure iodide. In another embodiment, the "pure iodide" refers to about 95 to 100% purity. In another embodiment, the "pure iodide" refers to about 90% to 100% purity. In another embodiment, the "pure iodide" refers to about 85% to 100% purity. In another embodiment, the "pure iodide" refers to about 99% to 100%. In another embodiment, the pure iodide refers to about 98% to 100%. In another embodiment, the pure iodide refers to about 97% to 100%.

In one embodiment, this invention is directed to iodide compound represented by the formula R—I having purity of between about 99% to 100%, prepared according to the process of this invention, wherein R is saturated or unsaturated, linear or branched, substituted or unsubstituted alkyl, substituted or unsubstituted aryl, saturated or unsaturated, substituted or unsubstituted mono- or poly-carbocyclic or heterocyclic ring. In another embodiment, R is saturated, linear or branched, substituted or unsubstituted alkyl, substituted or unsubstituted aryl, saturated or unsaturated, substituted or unsubstituted mono- or poly-carbocyclic or heterocyclic ring. In another embodiment, this invention is directed to iodide compound represented by the formula R—I having purity of between about 98% to 100%, prepared according to the process of this invention. In another embodiment, this invention is directed to iodide compound represented by the formula R—I having purity of between about 90% to 100%, prepared according to the process of this invention. In another embodiment, this invention is directed to iodide compound represented by the formula R—I having purity of between about 95% to 100%, prepared according to the process of this invention. In another embodiment, this invention is directed to iodide compound represented by the formula R—I having purity of between about 85% to 100%, prepared according to the process of this invention. In another embodiment, this invention is directed to iodide compound represented by the formula R—I having purity of between about 97% to 100%, prepared according to the process of this invention.

In one embodiment, this invention is directed to iodide compound represented by the formula R—I having purity of between about 99% to 100%. In another embodiment, this invention is directed to iodide compound represented by the formula R—I having purity of between about 98% to 100%. In another embodiment, this invention is directed to iodide compound represented by the formula R—I having purity of between about 90% to 100%. In another embodiment, this invention is directed to iodide compound represented by the formula R—I having purity of between about 95 to 100%. In another embodiment, this invention is directed to iodide compound represented by the formula R—I having purity of between about 85% to 100%.

In one embodiment, the process of this invention provides a process for the preparation of R—I with a yield of between about 60-100%. In another embodiment, the process of this invention provides a process for the preparation of R—I with a yield of between about 70-100%. In another embodiment, the process of this invention provides a process for the preparation of R—I with a yield of between about 80-100%. In another embodiment, the process of this invention provides a process for the preparation of R—I with a yield of between about 85-100%. In another embodiment, the process of this invention provides a process for the preparation of R—I with a yield of between about 90-100%. In another embodiment, the process of this invention provides a process for the preparation of R—I with a yield of between about 95-100%.

In one embodiment, this invention is directed to a process comprising a reaction between N-iodo reagent and R—COOH. In another embodiment the molar ratio between the N-iodo reagent/R—COOH is between 0.5 to 2 moles N-iodo reagent per 1 mol of R—COOH. In another embodiment the molar ratio between the N-iodo reagent/R—COOH is between 1 to 2 moles N-iodo reagent per 1 mol of R—COOH. In another embodiment the molar ratio between the N-iodo reagent/R—COOH is between 0.5 to 1.5 moles N-iodo reagent per 1 mol of R—COOH.

In one embodiment, this invention is directed to a process comprising a reaction between DIH and R—COOH. In another embodiment, the molar ratio between DIH/R—COOH is between 0.5 to 2 moles DIH per 1 mol of R—COOH. In another embodiment, the molar ratio between DIH/R—COOH is between 1 to 2 moles DIH per 1 mol of R—COOH. In another embodiment, the molar ratio between DIH/R—COOH is between 0.5 to 1.5 moles DIH per 1 mol of R—COOH.

In another embodiment, the molar ratio of the N-iodo reagent depends on the acids used. Alkylcarboxylic acid is converted into the corresponding iodide in good yield at 0.5:1 to 1.2:1 molar ratio DIH/R—COOH, while aromatic carboxylic acids required excess of DIH (1:1 to 2:1 molar ratio DIH/R—COOH).

In one embodiment this invention provides a process for the preparation of R—I. In another embodiment, the process of this invention is a radical reaction. In another embodiment all factors that promote radical reaction may stimulate the process of this invention.

In one embodiment, the process of this invention is initiated thermally. In another embodiment, the process of this invention is conducted at a temperature between about 50° C. and about 200° C. In another embodiment, the process of this invention is conducted at a temperature between about 70° C. and about 200° C. In another embodiment, the process of this invention is conducted at a temperature between about 80° C. and about 200° C. In another embodiment, the process of this invention is conducted at a temperature between about 90° C. and about 200° C. In another embodiment, the process of this invention is conducted at a temperature between about 100° C. and about 200° C. In another embodiment, the process of this invention is conducted at a temperature between about 80° C. and about 100° C. In another embodiment, the process of this invention is conducted at a temperature between about 70° C. and about 150° C. In another embodiment, the process of this invention is conducted at a temperature between about 80° C. and about 150° C. In another embodiment, the process of this invention is conducted at a temperature between about 90° C. and about 150° C. In another embodiment, the process of this invention is conducted at a temperature between about 100° C. and about 150° C.

In another embodiment, the process of this invention is conducted for between 1-24 h. In another embodiment, the process of this invention is conducted for between 1-10 h. In another embodiment, the process of this invention is conducted for between 5-10 h. In another embodiment, the process of this invention is conducted for between 6-10 h. In another embodiment, the process of this invention is conducted for between 7-10 h. In another embodiment, the process of this invention is conducted for between 8-10 h. In another embodiment, the process of this invention is conducted at a temperature between about 50° C. and about 200° C. for about 1 h to about 24 h. In another embodiment, the process of this invention is conducted at a temperature between about 70° C. and about 150° C. for about 1 h to about 24 h. In another embodiment, the process of this invention is conducted at a temperature between about 100° C. and about 150° C. for about 1 h to about 24 h. In another embodiment, the process of this invention is conducted at a temperature of between 50° C. and about 200° C. for about 1 h to about 5 h. In another embodiment, the process of this invention is conducted at a temperature of between 50° C. and about 200° C. for about 1 h to about 10 h. In another embodiment, the process of this invention is conducted at a temperature of between 50° C. and about 200° C. for about 1 h to about 15 h.

In one embodiment this invention provides a process for the preparation of R—I. In another embodiment, the process of this invention is a radical reaction. In another embodiment all factors that promote radical reaction may stimulate the process of this invention. Factors that promote radical reaction: heating, radiation, addition of radical initiators. The same factors promote the reaction of this invention. Some reagents (e.g. TEMPO) react with carbon-centered radicals to give nonreactive products. If addition of TEMPO inhibit reaction this fact indicate that the reaction is radical chain reaction. Addition of TEMPO inhibits iodo-de-carboxylation reaction and indicates that the reaction of this invention has a radical nature.

In one embodiment, the process of this invention is conducted under radiation. In one embodiment, the process of this invention is conducted under electromagnetic radiation. In one embodiment, the process of this invention is conducted under actinic radiation. In another embodiment, the radiation may be infrared (IR) radiation, visible radiation (light), microwave radiation, or ultraviolet (UV) radiation. In another embodiment, the electromagnetic radiation is visible light. In another embodiment, the process of this invention is conducted in the presence of electromagnetic radiation for about 1 h to about 5 h. In another embodiment, the process of this invention is conducted in the presence of electromagnetic radiation for about 1 h to about 5 h. In another embodiment, the process of this invention is conducted in the presence of electromagnetic radiation for about 1 h to about 10 h. In another embodiment, the process of this invention is conducted in the presence of electromagnetic radiation for about 1 h to about 15 h.

In one embodiment, the process of this invention is conducted in the presence of radical initiator. In another embodiment the radical initiators are substances that can produce radical species. Non limiting examples of radical species are azo compounds such as azobisisobutyronitrile (AIBN) or 1,1'-azobis(cyclohexanecarbonitrile) (ABCN), and organic peroxides such benzoyl peroxide. In another embodiment, the process of this invention is conducted in the presence of radical initiator for about 1 h to about 24 h.

In another embodiment, the process of this invention is conducted in the presence of ultrasound. In another embodiment, the process of this invention is conducted in the presence of microwave irradiation. In another embodiment, the process of this invention is conducted in the presence of radical initiator, electromagnetic radiation or combination thereof. In another embodiment, the process of this invention is conducted in the presence of radical initiator, ultrasound, electromagnetic radiation or combination thereof.

In another embodiment, the process of this invention is conducted in the presence of iodine catalyst. In another embodiment the iodine catalyst is organic iodide, inorganic iodide or molecular iodine or mixture thereof. In another embodiment the organic iodide is saturated, linear or branched, substituted or unsubstituted alkyl iodide, or substituted or unsubstituted aryl iodide. In another embodiment, the inorganic iodide is HI, ICl, NaI, KI, LiI, or any mixture thereof. In another embodiment, the iodine catalyst:carboxylic acid molar ratio is between 0.1 to 50%. In another embodiment, the iodine catalyst:carboxylic acid molar ratio is between 0.1 to 20%. In another embodiment, the iodine catalyst:carboxylic acid molar ratio is between 0.1 to 2 mole %. In another embodiment, the organic iodide catalyst may be the product of the iododecarboxylation reaction or play role solvent or co-solvent of the iododecarboxylation reaction. The preferred iodine catalyst is molecular iodine.

The term "radical" refer in this invention to molecular entities possessing an unpaired electron, such as $H_3C.$, $C_6H_5.$, I.. (In these formulae the dot, symbolizing the unpaired electron, should be placed so as to indicate the atom of highest spin density, if this is possible). Depending on the nature of the core atom that possesses an unpaired electron, the radicals can be described as carbon-, oxygen-, nitrogen-, iodine-centered radicals. Subclasses are e.g. alkyl (e.g. propyl $CH_3CH_2CH_2.$), aryl (e.g. phenyl $C_6H_5.$), acyloxyl (e.g. $RC(=O)O.$), aminoxyl (e.g. TEMPO), acylaminyl (e.g. $RC(=O)NR.$), carbon-centered radical R. derived formally by removal of carboxyl group from R—COOH.

The term "radiation" refers in one embodiment to the energy that is radiated or transmitted in the form of rays or waves or particles. Electromagnetic radiation refers to radiation consisting of waves of energy associated with electric and magnetic fields resulting from the acceleration of an electric charge. Actinic radiation refers to electromagnetic radiation that can produce photochemical reactions. Ultrasound refers to cyclic mechanical vibrations with a frequency greater than 20 kilohertz (20,000 hertz).

Ultraviolet radiation refers to electromagnetic radiation with wavelengths 100 to 400 nm.

Visible radiation (light, visible light) refers to electromagnetic radiation with wavelengths 400 to 780 nm.

Infrared radiation refers to electromagnetic radiation with wavelengths 780 to 20000 nm. Microwave radiation refers to electromagnetic radiation with wavelengths 2 to 1000 mm.

Devices serving as a source of the electromagnetic radiation include a mercury lamp, a xenon lamp, a carbon arc lamp, a tungsten lamp, a fluorescent lamp, light-emitting diode (LED), and sunlight, and the like.

Tungsten lamp refers to incandescent lamp that generates light by passing an electric current through a thin filament wire (usually of wolfram) until it is extremely hot. The lamps are often filled by a halogen gas such as iodine and bromine that allow filaments to work at higher temperatures and higher efficiencies.

Light-emitting diode (LED) refers to a semiconductor (often a combination of gallium, arsenic, and phosphorous or gallium and nitrogen) containing an n region (where electrons are more numerous than positive charges) separated from a p region (where positive charges are more numerous than negative charges). Upon application of a voltage, charges move and emission of ultraviolet, visible, or infrared radiation is produced each time a charge recombination takes place. Although an LED emits incoherent monochromatic light, normally a very narrow frequency range is obtained.

The term "about" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to about 5%, up to about 10% or up to about 20% of a given value.

An "alkyl" refers, in one embodiment, to an univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: The groups $RCH_2$—, $R_2CH$— (R≠H), and $R_3C$— (R≠H) are primary, secondary and tertiary alkyl groups respectively, In another embodiment alkyl refers to an unsaturated hydrocarbon, including straight-chain, branched-chain. In one embodiment, the alkyl group has 1-20 carbons. In another embodiment, the alkyl group has 10-20 carbons. In another embodiment, the alkyl group has 1-6 carbons. In another embodiment, the alkyl group has 2-7 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or unsubstituted by one or more groups selected from halogen, phenyl, aryl, haloalkyl, protected hydroxyl, cyano, azide, carboxylic acid, aldehyde, alkoxy, carbonyl, amido, alkylamido, nitro, protected amino, alkylamino, protected thio and/or thioalkyl.

An "aryl" group refers, in one embodiment, to groups derived from arenes by removal of a hydrogen atom from a ring carbon atom. In another embodiment an aryl group refers to an aromatic group having at least one carbocyclic aromatic group or heterocyclic aromatic group, which may be unsubstituted or substituted by one or more groups selected from halogen, aryl, haloalkyl, protected hydroxyl, cyano, azide, carboxylic acid, aldehyde, alkoxy, carbonyl, amido, alkylamido, nitro, protected amino, alkylamino, protected thio and/or thioalkyl. Nonlimiting examples of aryl groups are phenyl, biphenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "mono- or poly-carbocyclic ring" refers to in one embodiment to cycloalkyl groups (Univalent groups derived from cycloalkanes by removal of a hydrogen atom from a ring carbon atom) In another embodiment, refers to a saturated or unsaturated mono-ring or poly-carbocyclic rings consisting of the carbon and hydrogen elements. In one embodiment, the poly-carbocyclic rings are 2-7 fused rings. In another embodiment, the poly-carbocyclic rings are 2-4 fused rings. In another embodiment, the poly-carbocyclic rings are 2-7 rings attached by a single bond or a double bond. In another embodiment, the poly-carbocyclic ring is combination of fused rings and rings which are attached by a single bond. Non limiting examples of mono or poly-carbocyclic ring are phenyl, biphenyl, cycloheptane, cyclohexane, cyclopentane, cyclobutane, naphthalene, norcholane, and cyclopropane. In another embodiment, the mono- or poly-carbocyclic ring may be unsubstituted or substituted by one or more groups selected from halogen, alkyl, aryl, haloalkyl, protected hydroxyl, cyano, azide, carboxylic acid, aldehyde, alkoxy, carbonyl, amido, alkylamido, nitro, protected amino, alkylamino, protected thio- and/or thioalkyl.

A "mono- or poly-heterocyclic ring" refers to a heterocyclyl group which is formed by removing a hydrogen atom from any ring atom of a heterocyclic compound. In another embodiment refers to heteroaryl group which derives from heteroarenes by removal of a hydrogen atom from any ring atom; an alternative term is hetaryl. In another embodiment refers to a saturated or unsaturated mono-ring or poly-cyclic rings consisting of carbon, hydrogen and at least one of nitrogen, sulfur, oxygen, phosphorous or combination thereof. In one embodiment, the poly-heterocyclic rings are 2-7 fused rings. In another embodiment, the poly-heterocyclic rings are 2-4 fused rings. In another embodiment, the poly-heterocyclic rings are 2-7 rings attached by a single bond. In another embodiment, the poly-heterocyclic ring is combination of fused rings and rings which are attached by a single bond. Non limiting examples of mono or poly-heterocyclic ring are 4-pyridyl, pyrrolidin-1-yl, pyrrolidin-2-yl, pyridyl, bi-pyridyl, piperidyl, E.g. 2-pyridyl (pyridin-2-yl), indol-1-yl and quinoline. In another embodiment, the mono- or poly-heterocyclic ring may be unsubstituted or substituted by one or more groups selected from halogen, alkyl, aryl, haloalkyl, protected hydroxyl, cyano, azide, carboxylic acid, aldehyde, alkoxy, carbonyl, amido, alkylamido, nitro, protected amino, alkylamino, protected thio and/or thioalkyl.

An "amide" refers, in one embodiment, to a derivative of oxoacid $R_kE(=O)_l(OH)_m$ ($l \neq 0$) in which an acidic hydroxy group has been replaced by an amino or substituted amino group. Compounds having one or two acyl groups on a given nitrogen are generically included and may be designated as primary and secondary amides, respectively. Non limiting examples of the amides include carboxamides (benzamide, secondary amide, imides, lactams, peptides etc.), phosphoramides (phenylphosphonamidic acid), and sulfonamides (N-methanesulfonamide).

A "carboxamide" refers, in one embodiment, to amides of carboxylic acids, having the structure $RC(=O)NH_2$.

A "diacylamine" refers, in one embodiment, to a compounds having two acyl groups substituted on ammonia or a primary amine: acyl-NH-acyl. They are also known as secondary amides and, especially the cyclic examples derived from diacids, as imides. E.g. $[RC(=O)]_2NH$, $RS(=O)_2NHC(=O)R$.

An "acyl" group is formed by removing one or more hydroxy groups from oxoacids that have the general structure $R_kE(=O)_l(OH)_m$ ($l \neq 0$), and replacement analogues of such acyl groups. E.g. $CH_3C(=O)-$, $CH_3C(=NR)-$, $CH_3C(=S)-$, $PhS(=O)_2-$, $HP(=N)-$, $R_2P(=O)-$.

A "lactam" refers, in one embodiment, to a cyclic amide of amino carboxylic acid, for example having a 1-azacycloalkan-2-one structure, or analogues having unsaturation or heteroatoms replacing one or more carbon atoms of the ring.

A "peptide" refers, in one embodiment, to amide derived from two or more amino carboxylic acid molecules (the same or different) by formation of a covalent bond from the carbonyl carbon to the nitrogen atom of another with formal loss of water. The term is usually applied to structures formed from α-amino acids, but it includes those derived from any amino carboxylic acid; a peptide presented as $H_2N-CHR-C(=O)-[NH-CHR-C(=O)]_n-OH$ (R may be any organyl group, commonly but not necessarily one found in natural amino acids).

A "phosphoramide" refers, in one embodiment, to a compound in which one or more of the OH groups of phosphoric acid have been replaced with an amino or substituted amino group; commonly confined to the phosphoric triamides, $P(=O)(NH_2)_3$, since replacement of one or two OH groups produces phosphoramidic acids: $P(=O)(OH)(NH_2)_2$, $P(=O)(OH)_2(NH_2)$.

A "sulfonamide" refers, in one embodiment, to an amide of sulfonic acids: $RS(=O)_2NHR'$. E.g. $PhS(=O)_2NHCH_3$ N-methylbenzenesulfonamide. A sulfonamide includes a "sultam". A "sultam" refers, in one embodiment to a sulfonamide which the S—N bond is part of a ring.

A "carbamate" refers, in one embodiment, to salts or esters of carbamic acid, $H_2NC(=O)OH$, or of N-substituted carbamic acids: $RHNC(=O)OR'$, (R'=hydrocarbyl or a cation).

An "ureide" refers, in one embodiment, to N-acyl or N,N-diacyl ureas; $H_2N-C(=O)-NH-C(=O)-R$ or $R-C(=O)-NH-C(=O)-NH-C(=O)-R$.

A nitramine refers, in one embodiment to an amines substituted at N with a nitro group (a contracted form of N-nitroamines); they are thus amides of nitric acid, and the class is composed of nitramide, $O_2NNH_2$, and its derivatives formed by substitution.

A "carboxylic acid" refers, in one embodiment, to oxoacids having the structure $RC(=O)OH$.

The following examples are presented in order to more fully illustrate the preferred embodiments of the invention. They should in no way, however, be construed as limiting the broad scope of the invention.

EXAMPLES

Experimental Details

Reagents:
trans-2-Phenyl-1-cyclopropanecarboxylic acid was purchased from TCI. N-Boc-4-piperidineacetic, 1-Boc-piperidine-4-carboxylic, and 1-Boc-azetidine-3-carboxylic acids were purchased from Chem-Impex International. 4-Methoxycarbonylcubanecarboxylic acid was purchased from Boron Molecular. All other reagents and solvents were purchased from Aldrich Chemical Company unless specified otherwise and used without further purification. 3α,7α,12α-Triformyloxy-5β-cholanic and 3α,12α-diformyloxy-5β-cholanic acids were prepared from cholic and deoxycholic acids according to published procedure (Steroids 2005, v. 70, 681). 1,4-Cubanedicarboxylic and 4-iodocubanecarboxylic acids were prepared from the corresponding methyl esters according to published procedure (Thermochimica Acta 2010, v. 499, 15).

Techniques:
All reactions were run under nitrogen atmosphere in non flame dried glassware. Mounted beneath the reaction flask 500 W tungsten lamp was used for irradiation and heat of the reaction mixture. Conversions were determined by $^1$H NMR, and yields of isolated product refer to products with more than 95% purity by $^1$H NMR. Flash column chromatography was performed employing 63-200 μm silica gel 60 according to standard techniques (J. Org. Chem. 1978, v. 43, 2923).

Analytical Methods:
For TLC analysis, Merck precoated TLC plates (silica gel 60 $F_{254}$ on glass plates, 0.25 mm) were used. NMR spectra were recorded on a Bruker AM-400 ($^1$H at 400 MHz, $^{13}$C at 100 MHz) instruments using $CDCl_3$ (unless otherwise stated) as a solvent. Data are reported as follows: chemical shift in ppm relative to internal TMS, multiplicity, coupling constant in Hz and integration. Compounds described in the literature were characterized by comparing their $^1$H and/or $^{13}$C NMR spectra to the previously reported data. New compounds were further characterized by high-resolution mass spectra.

The following abbreviations are used:
ABCN=1,1'-azobis(cyclohexanecarbonitrile)
AIBN=azobisisobutyronitrile
Alk=alkyl
Ar=aryl
Bn=benzyl
Boc=tert-butoxycarbonyl protective group
Bz=benzoyl
Cbz=benzyloxycarbonyl protective group
d=doublet
DCE=1,2-dichloroethane
DCM=dichloromethane
DIH=1,3-Diiodo-5,5-dimethylhydantoin
DMF=N,N-dimethylformamide
FL=fluorescent lighting
Freon® 112=1,1,2,2-tertrachlorodifluoroethane
Freon® 113=1,1,2-trichlorotrifluoroethane
m=multiplet
"—N—I"=N-iodo reagent
NIS=N-iodosuccinimide NISac=N-iodosaccharine
NL=dark
NMP=1-methyl-2-pyrrolydinone
NMR=nuclear magnetic resonance
rt=room temperature
s=singlet
t=triplet
TEMPO=2,2,6,6-tetramethyl-1-piperidinyloxy, free radical
TICA=triiodoisocyanuric acid
TIG=2,4,6,8-tetraiodoglycoluril
TL=tungsten lamp irradiation
hv=electromagnetic radiation
Δ=heating

Example 1

Solvent Effect of Iodo-De-Carboxylation

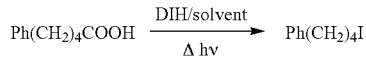

A mixture of $Ph(CH_2)_4COOH$ (0.25 mmol), DIH (0.25 mmol), and solvent (1 mL) was refluxed (Δ) for 1 h under irradiation with 500 W tungsten lamp (TL). Conversion degree was determined by $^1H$ NMR spectra of the reaction mixture.

The solvent effect is presented in Table 1:

TABLE 1

| entry | solvent | conversion, % |
|---|---|---|
| 1 | PhCl | 100 |
| 2 | DCE | 83 |
| 3 | DCE | 20 |
| 4 | EtOAc | 62 |
| 5 | BuOAc | 59 |
| 6 | MeCN | 59 |
| 7 | MeNO$_2$ | 53 |
| 8 | hepfane | 46 |
| 9 | cyclohexane | 45 |
| 10 | CCl4 | 40 |

Entry 3 gives example of radical trap effect when the reaction was provided in the presence of 10 mol % of TEMPO.

Example 2

Effect of Radiation and N-Iodoamide/Acid Ratio

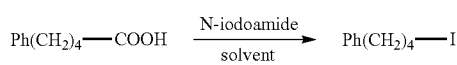

A mixture of $Ph(CH_2)_4COOH$ (1 mmol), N-iodoamide (1-3 equiv), and solvent (4 mL) was refluxed (Δ) in the dark (NL) or under irradiation with 500 W tungsten lamp (TL) or under fluorescent room lighting (FL). Conversion degree was determined by $^1H$ NMR spectra of the reaction mixture.

The radiation and N-iodoamide/acid ratio effects are presented in Table 2:

TABLE 2

| entry | reaction conditions | conversion, % | | | |
|---|---|---|---|---|---|
| | | 1 h | 4 h | 8 h | 24 h |
| 1 | 1 equiv DIH/ Ph(CH$_2$)$_4$COOH DCE, TL | 11 | 48 | 60 | 60 |
| 2 | 2 equiv DIH/ Ph(CH$_2$)$_4$COOH DCE, FL | 4 | 16 | 32 | 48 |
| 3 | 2 equiv DIH/ 0.2 equiv I$_2$/ Ph(CH$_2$)$_4$COOH DCE, FL | 17 | 42 | 57 | |
| 4 | 2 equiv DIH/ Ph(CH$_2$)$_4$COOH DCE, TL | 47 | 98 | 100 | |
| 5 | 2 equiv DIH/ 0.2 equiv I$_2$/ Ph(CH$_2$)$_4$COOH DCE, TL | 89 | | | |
| 6 | 3 equiv DIH/ Ph(CH$_2$)$_4$COOH DCE, TL | 100 | | | |
| 7 | 3 equiv DIH/ Ph(CH$_2$)$_4$COOH DCE, NL | 7 | 24 | 33 | 46 |
| 8 | 1.5 equiv DIH/ Ph(CH$_2$)$_4$COOH PhCl, FL | 70 | 73 | 73 | |
| 9 | 1.5 equiv DIH/ Ph(CH$_2$)$_4$COOH PhCl, TL | 74 | 92 | 95 | |
| 10 | 3 equiv DIH/ Ph(CH$_2$)$_4$COOH PhCl, NL | 100 | | | |
| 110 | 1 equiv NIS/ Ph(CH$_2$)$_4$COOH DCE, TL | 38 | 61 | 63 | 63 |
| 121 | 1.5 equiv NIS/ Ph(CH$_2$)$_4$COOH DCE, TL | 62 | 91 | 100 | |
| 13 | 2 equiv NIS/ Ph(CH$_2$)$_4$COOH DCE, TL | 81 | 100 | | |
| 14 | 3 equiv NIS/ Ph(CH$_2$)$_4$COOH PhCl, NL | 85 | 100 | | |

Example 3

Radical Iodo-De-Carboxylation Induced by N-Iodo Amides

General Procedure

Procedure:

A mixture of R—COOH (1 mmol), N-iodo amide (1-4 equiv), and solvent (3-6 mL) was refluxed (Δ) for 1-24 h in the dark (NL) or under irradiation with 500 W tungsten lamp (TL) or under fluorescent room lighting (FL).

Treatment:

The reaction mixture was cooled to rt, and washed with aq NaHSO$_3$ and NaHCO$_3$ to destroy excess of iodination agent and dissolve unreacted carboxylic acid. The organic solution was dried (Na$_2$SO$_4$), filtered through short silica or alumina pad and concentrated in vacuo to give iodide R—I.

Purification:

Optionally, the iodide R—I was further purified by crystallization (if the iodide is crystalline compound), or rectification (if the iodide is liquid compound). Analytical sample of the product was purified by column chromatography.

$$\text{Alk}\text{—COOH} \xrightarrow{\text{N-iodoamide}} \text{Alk}\text{—I}$$

A mixture of Alk-COOH (1 mmol), N-iodo amide (1-3 equiv), and solvent (4 mL) was refluxed (Δ) in the dark (NL) or under irradiation with 500 W tungsten lamp (TL), or under fluorescent room lighting (FL).

The results are presented in Table 3:

TABLE 3

| entry | reaction conditions | Alk-I isolated yield |
|---|---|---|
| 1 | 2 equiv DIH DCE, TL 15 h | Ph(CH$_2$)$_4$—I 85% |
| 2 | 3 equiv DIH PhCl, NL 1 h | 88% |
| 3 | 3 equiv DIH PhCl, FL 1 h | 91% |
| 4 | 2 equiv NIS DCE, TL 15 h | 73% |
| 5 | 2.4 equiv DIH DCE, TL 2 h | Ph(CH$_2$)$_3$—I 90% |
| 6 | 3 equiv DIH DCE, TL 24 h | F(CF$_2$)$_{13}$—I 78% |
| 7 | 1.5 equiv NIS DCE, TL 24 h | 28% |
| 8 | 2.4 equiv DIH DCE, TL 2 h | Ac—N(piperidine)—I, 87% |
| 9 | 1.5 equiv NIS DCE, TL 4 h | 75% |
| 10 | 2.4 equiv DIH DCE, TL 3 h | Boc—N(azetidine)—I, 78% |
| 11 | 2.4 equiv DIH PhCl, FL 1 h | 73% |
| 12 | 2.4 equiv DIH DCE, TL 2 h | I—(bicyclic)—I, 93% |
| 13 | 2.5 equiv DIH DCE, TL 4 h | 76% |
| 14 | 2.2 equiv DIH DCE, TL 3 h | PhCH$_2$CHI$_2$ 75% |
| 15 | 2.2 equiv DIH DCE, TL 3 h | BuCHI$_2$ 71% |
| 16 | 2.4 equiv DIH DCE, TL 3 h | BuCHBrI 81% |
| 17 | 2.4 equiv DIH DCE, TL 2 h | Ph-cyclopropyl-I, 66% |
| 18 | 1 equiv DIH DCE, TL 8 h | m-O$_2$NC$_6$H$_4$CH$_2$—I 84% |
| 19 | 2 equiv DIH DCE, TL 8 h | 88% |
| 20 | 3 equiv DIH DCE, FL 7 h | 91% |
| 21 | 1 equiv NIS DCE, TL 8 h | 76% |
| 22 | 2.4 equiv DIH DCE, TL 2 h | c-C$_6$H$_{11}$(CH$_2$)$_2$—I 80% |
| 23 | 2 equiv DIH DCE, TL 2 h | H(CH$_2$)$_{17}$—I 73% |
| 24 | 2.4 equiv DIH DCE, TL 2 h | MeOOC-CH(NHCbz)-CH$_2$CH$_2$-I (S), 32% |
| 25 | 3 equiv DIH DCE, TL 2 h | Boc—N(piperidine)—CH$_2$I, 77% |
| 26 | 2.4 equiv DIH DCE, TL 2 h | Boc—N(piperidine)—I, 80% |
| 27 | 3 equiv DIH DCE, FL 7 h | 87% |
| 28 | 2.4 equiv DIH PhCl, FL 1 h | 96% |
| 29 | 2.4 equiv DIH DCE, TL 2 h | MeOOC-(bicyclic)-I, 93% |
| 30 | 1.5 equiv NIS DCE, TL 4 h | 93% |
| 31 | 3 equiv DIH DCE, FL 7 h | 97% |
| 32 | 2.4 equiv DIH DCE, TL 2 h | (cyclobutane with I and COOEt), 91% |
| 33 | 2.4 equiv DIH DCE, TL 2 h | (cholestane derivative with HCOO and I), 83% |

TABLE 3-continued

| entry | reaction conditions | Alk-I isolated yield |
|---|---|---|
| 34 | 2.4 equiv DIH<br>DCE, TL 2 h | 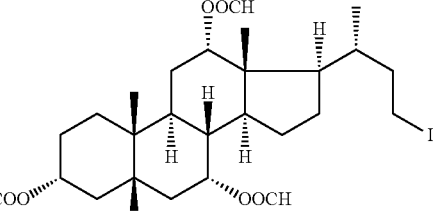<br>87% |

Entry 13: AlkCOOH=1,4-cubanedicarboxylic acid.

Entry 14: AlkCOOH=PhCH$_2$CH(COOH)$_2$.

Entry 15: AlkCOOH=BuCH(COOH)$_2$.

Entries 1-4: (4-Iodobutyl)benzene: $^1$H NMR δ 7.31 (m, 2H), 7.21 (m, 3H), 3.22 (t, J=7 Hz, 2H, CH$_2$—I), 2.66 (t, J=8 Hz, 2H), 1.87 (m, 2H), 1.77 (m, 2H); $^{13}$C NMR δ 141.9, 128.5, 126.0, 34.9, 33.0, 32.3, 6.9 (C—I).

Entry 5: (3-Iodopropyl)benzene: $^1$H NMR δ 7.31 (m, 2H), 7.22 (m, 3H), 3.18 (t, J=7 Hz, 2H, CH$_2$I), 2.74 (t, J=7 Hz, 2H), 2.14 (m, 2H); $^{13}$C NMR δ 140.5, 128.69, 128.63, 126.3, 36.3, 35.0, 6.5 (C—I).

Entries 6-7: Perfluorotridecyl iodide: $^{19}$F NMR δ −60.4 (2F, CF$_2$I), −82 (3F), −114.3 (2F), −122.1 (2F), −122.9 (10F), −123.1 (2F), −123.9 (2F), −127.3 (2F).

Entries 8-9: 1-Acetyl-4-iodopiperidine: $^1$H NMR δ 4.48 (dddd, J=6, 6, 6, 6 Hz, 1H), 3.72 (m, 1H), 3.55 (m, 1H), 3.49 (ddd, J=12, 6, 6 Hz, 1H), 3.36 (ddd, J=12, 6, 6 Hz, 1H), 2.07 (s, 3H), 2.02 (m, 4H); $^{13}$C NMR δ 169.0, 46.4, 41.5, 37.8, 37.1, 26.9 (C—I), 21.5.

Entries 10-11: 1-Boc-3-Iodoazetidine: $^1$H NMR δ 4.63 (dd, J=6 Hz, 2H), 4.46 (m, 1H), 4.28 (dd, J=5 Hz, 2H), 1.43 (s, 9H); $^{13}$C NMR δ 155.7, 80.3, 61.7, 28.4, 2.7 (C—I).

Entries 12-13: 1,4-Diiodocubane: $^1$H NMR δ 4.40 (s); $^{13}$C NMR δ 57.6; 35.8 (C—I).

Entry 14: (2,2-Diiodoethyl)benzene: $^1$H NMR δ 7.34 (m, 3H), 7.25 (m, 2H), 5.11 (t, 1H), 3.76 (d, J=7 Hz, 2H); $^{13}$C NMR δ 139.9, 129.0, 128.8, 127.7, 54.5, −25.5 (C—I).

Entry 15: 1,1-Diiodopentane: $^1$H NMR δ 5.11 (t, J=7 Hz, 1H), 2.36 (m, 2H), 1.38 (m, 4H), 0.93 (m, 3H); $^{13}$C NMR δ 48.2, 34.1, 21.0, 14.0, −25.0 (C—I).

Entry 16: 1-Bromo-1-iodopentane: $^1$H NMR δ 5.53 (t, 1H), 2.38 (m, 2H), 1.47 (m, 2H), 1.37 (m, 2H), 0.93 (t, 3H); $^{13}$C NMR δ 47.0, 32.1, 21.3, 14.0, 12.9.

Entry 17: trans-2-Phenyl-1-cyclopropyl iodide: $^1$H NMR δ 7.29 (m, 2H), 7.21 (m, 1H), 7.06 (d, 2H), 2.56 (m, 1H), 2.33 (m, 1H), 1.49 (m, 1H), 1.41 (m, 1H); $^{13}$C NMR δ 140.4, 128.7, 126.6, 125.9, 27.9, 20.0, −13.1 (C—I). cis-2-Phenyl-1-cyclopropyl iodide (8% yield) was also isolated from the reaction mixture: $^1$H NMR δ 7.37-7.19 (m, 5H), 2.96 (m, 1H), 2.08 (m, 1H), 1.69 (m, 1H), 1.26 (m, 1H); $^{13}$C NMR δ 139.4, 129.1, 128.1, 127.0, 29.8, 15.0, −4.9 (C—I).

Entries 18-21: 3-Nitrobenzyl iodide: $^1$H NMR δ 8.24 (s, 1H), 8.11 (d, J=8 Hz, 1H), 7.70 (d, J=8 Hz, 1H), 7.49 (t, J=8 Hz, 1H), 4.49 (s, 2H, CH$_2$I); $^{13}$C NMR δ 148.6, 141.6, 134.9, 130.0, 123.7, 122.9, 2.3 (C—I).

Entry 22: (2-Iodoethyl)cyclohexane: $^1$H NMR δ 3.21 (t, J=8 Hz, 2H, CH$_2$I), 1.72 (m, 7H), 1.38 (m, H), 1.23 (m, 3H), 0.91 (m, 2H); $^{13}$C NMR δ 41.4, 38.6, 32.6, 26.6, 26.2, 5.3 (CI).

Entry 23: 1-Iodoheptadecane: $^1$H NMR δ 3.19 (t, J=7 Hz, 2H, CH$_2$I), 1.82 (qn, 2H), 1.39 (m, 1H), 1.26 (bs), 0.88 (t, J=7 Hz, 3H); $^{13}$C NMR δ 33.5, 31.8, 30.4, 29.59, 29.55, 29.51, 29.45, 29.32, 29.26, 28.4, 22.6, 14.0, 7.3 (C—I).

Entry 24: (S)-methyl 2-(benzyloxycarbonyl)amido-4-iodobutanoate: $^1$H NMR: δ 7.36 (m, 5H), 5.32 (br d, J 6 Hz, 1H), 5.12 (s, 2H), 4.44 (br m, 1H), 3.77 (s, 3H), 3.17 (t, J 7 Hz, 2H), 2.45 (m, 1H), 2.23 (m, 1H); $^{13}$C NMR: δ 171.7, 155.9, 136.0, 128.5, 128.2, 128.1, 60.4, 54.6, 62.7, 36.7, −0.68.

Entry 25: 1-Boc-4-(Iodomethyl)piperidine: $^1$H NMR δ 4.11 (br d, J=13 Hz, 2H), 3.09 (d, J=7 Hz, 2H), 2.68 (br t, J=12 Hz, 2H,), 1.82 (br d, J=13 Hz, 2H,), 1.62 (m, 1H), 1.45 (s, 9H), 1.14 (ddd, J=25, 13, 4 Hz, 2H); $^{13}$C NMR δ 154.8, 79.6, 43.8, 38.8, 32.7, 28.6, 13.6 (C—I).

Entries 26-28: 1-Boc-4-Iodopiperidine: $^1$H NMR δ 4.44 (m, 1H, CHI), 3.58 (m, J=14, 4 Hz, 2H), 3.3 (dt, J=6, 4 Hz, 2H), 2.01 (m, 4H), 1.45 (s, 9H); $^{13}$C NMR δ 154.8, 79.9, 44.0, 37.5, 28.6, 27.8.

Entries 29-31: Methyl 4-iodocubanecarboxylate: $^1$H NMR δ 4.39 (m, 3H), 4.30 (m, 3H), 3.71 (s, 3H); $^{13}$C NMR δ 172.0, 56.3, 55.0, 51.8, 50.4, 36.3 (C—I).

Entry 32: Ethyl 1-iodocyclobutanecarboxylate: $^1$H NMR δ 4.20 (q, 2H), 2.82 (m, 2H), 2.57 (m, 2H), 2.17 (m, 1H), 1.86 (m, 1H), 1.26 (t, 3H); $^{13}$C NMR δ 173.4, 61.9, 39.3, 29.7, 18.5, 13.8.

Entry 33: 3α,12α-Diformyloxy-5β-23-iodo-24-norcholane: $^1$H NMR δ 8.12 (s, 1H), 8.02 (s, 1H), 5.24 (s, 1H), 4.83 (m, 1H), 3.17 (m, 2H), 2.05-0.95 (m), 0.92 (s, 3H), 0.83 (d, J=6 Hz, 3H), 0.76 (s, 3H); $^{13}$C NMR δ 160.8, 160.6, 76.1, 74.2, 49.4, 47.4, 45.2, 41.9, 40.1, 36.7, 35.7, 34.8, 34.3, 32.2, 27.5, 26.9, 26.6, 26.0, 25.9, 23.6, 23.6, 23.1, 17.1, 12.5, 5.0.

Entry 34: 3α,7α,12α-Triformyloxy-5β-23-iodo-24-norcholane: $^1$H NMR δ 8.15 (s, 1H), 8.09 (s, 1H), 8.02 (s, 1H), 5.27 (bs, 1H), 5.07 (bs, 1H), 4.71 (m, 1H), 3.28 (m, 1H), 3.06 (dd, J=8, 8 Hz, 1H), 2.20-1.25 (m), 1.11 (m, 2H), 0.94 (s, 3H), 0.84 (d, J=6 Hz, 3H), 0.77 (s, 3H); $^{13}$C NMR δ 160.7, 160.6, 75.4, 73.9, 70.8, 47.3, 45.3, 43.1, 40.9, 39.9, 37.9, 36.6, 34.7, 34.6, 34.4, 31.5, 28.7, 27.3, 26.7, 25.7, 22.9, 22.5, 17.2, 12.3, 4.8 (C—I).

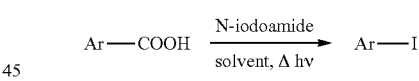

A mixture of Ar—COOH (1 mmol), N-iodo amide (1.5-4 equiv), and solvent (4 mL) was refluxed (Δ) under irradiation with 500 W tungsten lamp (TL) or under fluorescent room lighting (FL).

The results are presented in the following Table 4:

| entry | reaction conditions | Ar—I isolated yield |
|---|---|---|
| 1 | 4 equiv DIH<br>DCE, TL 15 h | 2-ClC6H4—I<br>82% |
| 2 | 3 equiv DIH<br>DCE, TL 15 h | 3-ClC$_6$H$_4$—I<br>33% |
| 3 | 2.4 equiv DIH<br>PhCl, FL 24 h | 4-ClC$_6$H$_4$—I<br>31% |
| 4 | 3 equiv DIH<br>DCE, TL 15 h | 2-BrC$_6$H$_4$—I<br>95% |
| 5 | 3 equiv DIH<br>DCE, TL 15 h | 3-BrC$_6$H$_4$—I<br>41% |
| 6 | 2 equiv DIH<br>DCE, TL 15 h | 4-BrC$_6$H$_4$—I<br>12% |
| 7 | 2 equiv DIH<br>DCE, TL 15 h | 2-IC$_6$H$_4$—I<br>80% |

-continued

| entry | reaction conditions | Ar—I isolated yield |
|---|---|---|
| 8 | 2 equiv NIS DCE, TL 15 h | 80% |
| 9 | 2.4 equiv DIH PhCl, FL 24 h | 80% |
| 10 | 3 equiv DIH DCE, TL 15 h | 3-IC$_6$H$_4$—I 47% |
| 11 | 2 equiv DIH DCE, TL 15 h | 4-IC$_6$H$_4$—I 52% |
| 12 | 3 equiv DIH DCE, TL 15 h | 2,4-Cl$_2$C$_6$H$_4$—I 47% |
| 13 | 3 equiv DIH PhCl, TL 24 h | 2-O$_2$NC$_6$H$_4$—I 72% |
| 14 | 3 equiv DIH PhCl, FL 24 h | 3-O$_2$NC$_6$H$_4$—I 48% |
| 15 | 3 equiv DIH PhCl, TL 24 h | 4-O$_2$NC$_6$H$_4$—I 70% |
| 16 | 3 equiv DIH DCE, TL 24 h | 2-MeOOCC$_6$H$_4$—I 80% |
| 17 | 2.4 equiv DIH PhCl, FL 24 h | 1-iodonaphthalene 47% |
| 18 | 3 equiv DIH DCE, TL 24 h | 4-PhC$_6$H$_4$—I 61% |
| 19 | 1.5 equiv NIS DCE, TL 24 h | 50% |
| 20 | 2.4 equiv DIH DCE, TL 15 h | 2-MeC$_6$H$_4$—I 28% |
| 21 | 3 equiv DIH PhCl, FL 18 h | 3-MeC$_6$H$_4$—I 60% |
| 22 | 3 equiv DIH PhCl, TL 20 h | 2-MeOC$_6$H$_4$—I 21% |
| 23 | 3 equiv DIH PhCl, FL 24 h | 3-MeOC$_6$H$_4$—I 58% |

Entry 1: 2-Chloroiodobenzene: $^1$H NMR δ 7.86 (dd, J=8, 2 Hz, 1H), 7.45 (dd, J=8, 2 Hz, 1H), 7.27 (m, 1H), 6.95 (m, 1H); $^{13}$C NMR δ 140.4, 138.7, 129.5, 128.0, 98.3 (C—I).

Entry 2: 3-Chloroiodobenzene: $^1$H NMR δ 7.72 (t, J=2 Hz, 1H), 7.59 (m, $^1$H), 7.32 (m, 1H), 7.02 (t, J=8 Hz, 1H); $^{13}$C NMR δ 137.3, 135.8, 135.2, 131.1, 128.1, 94.2 (C—I).

Entry 3: 4-Chloroiodobenzene: $^1$H NMR δ 7.60 (d, J=9 Hz, 2H), 7.08 (d, J=9 Hz, 2H); $^{13}$C NMR δ 138.9, 134.4, 130.7, 91.3 (C—I).

Entry 4: 2-Bromoiodobenzene: $^1$H NMR δ 7.86 (t, J=8 Hz, 1H), 7.63 (d, J=8 Hz, 1H), 7.21 (d, J=8 Hz, 1H), 6.99 (t, J=8 Hz, 1H); $^{13}$C NMR δ 140.5, 132.9, 129.9, 129.6, 128.5, 101.3 (C—I).

Entry 5: 3-Bromoiodobenzene: $^1$H NMR δ 7.87 (t, J=2 Hz, 1H), 7.63 (d, J=8 Hz, 1H), 7.46 (d, J=8 Hz, 1H), 6.97 (t, J=8 Hz, 1H); $^{13}$C NMR δ 139.9, 136.2, 131.5, 130.9, 123.3, 94.6 (C—I).

Entry 6: 4-Bromoiodobenzene: $^1$H NMR δ 7.54 (dt, J=9 Hz, 2H), 7.23 (dt, J=9 Hz, 2H); $^{13}$C NMR δ 139.2, 133.6, 122.4, 92.2 (C—I).

Entries 7-9: 1,2-Diiodobenzene: $^1$H NMR δ 7.87 (m, 2H), 7.03 (m, 2H); $^{13}$C NMR δ 139.5, 129.3, 108.0 (C—I).

Entry 10: 1,3-Diiodobenzene: $^1$H NMR δ 8.06 (t, J=2 Hz, 1H), 7.67 (d, J=2 Hz, 1H), 7.65 (d, J=2 Hz, 1H), 6.83 (t, J=8 Hz, 1H); $^{13}$C NMR δ 145.3, 136.8, 131.7, 95.1 (C—I).

Entry 11: 1,4-Diiodobenzene: $^1$H NMR δ 7.41 (s); $^{13}$C NMR δ 139.5, 93.5 (C—I).

Entry 12: 2,4-Dichloroiodobenzene: $^1$H NMR δ 7.76 (d, J=9 Hz, 1H), 7.46 (d, J=2 Hz, 1H), 6.96 (dd, J=9, 2 Hz, 1H); $^{13}$C NMR δ 140.9, 139.6, 135.3, 129.4, 128.5, 95.6 (C—I).

Entry 13: 2-Nitroiodobenzene: $^1$H NMR δ 8.05 (dd, J=8, 1 Hz, 1H), 7.86 (dd, J=8, 1 Hz, 1H), 7.49 (m, 1H), 7.27 (m, 1H); $^{13}$C NMR δ 153.2, 142.1, 133.5, 129.2, 125.4, 86.3 (C—I).

Entry 14: 3-Nitroiodobenzene: $^1$H NMR δ 8.57 (t, J=2 Hz, 1H), 8.20 (d, J=8 Hz, 1H), 8.03 (d, J=8 Hz, 1H), 7.30 (dd, 1H); $^{13}$C NMR δ 148.6, 143.6, 132.5, 130.8, 122.9, 93.6 (C—I).

Entry 15: 4-Nitroiodobenzene: $^1$H NMR δ 7.95 (d, 2H), 7.91 (d, 2H); $^{13}$C NMR δ 147.9, 138.8, 125.0, 102.8 (C—I).

Entry 16: Methyl 2-iodobenzoate: $^1$H NMR δ 7.99 (dd, J=8, 1, 1H), 7.8 (d, J=8, 2, 1H), 7.39 (td, J=8, 1, 1H), 7.15 (td, J=8, 2, 1H,), 3.93 (s, 3H); $^{13}$C NMR δ 167.1, 141.5, 135.3, 132.8, 131.1, 128.0, 94.2 (C—I), 52.6.

Entry 17: 1-Iodonaphthalene: $^1$H NMR δ 8.09 (m, 2H), 7.84 (m, 1H), 7.77 (m, 1H), 7.58 (m, 1H), 7.52 (m, 1H), 7.18 (m, 1H); $^{13}$C NMR δ 137.6, 134.5, 134.3, 132.3, 129.1, 128.7, 127.9, 127.0, 126.9, 99.7 (C—I).

Entries 18-19: 4-Iodobiphenyl: $^1$H NMR δ 7.77 (m, 2H), 7.55 (m, 2H), 7.44 (m, 2H), 7.37 (m, 1H), 7.33 (m, 2H); $^{13}$C NMR δ 140.9, 140.2, 138.0, 129.2, 129.0, 127.8, 127.0, 93.2 (C—I).

Entry 20: 2-Iodotoluene: $^1$H NMR δ 7.81 (d, J=8 Hz, 1H), 7.24 (m, 2H), 6.87 (m, 1H), 2.43 (s, 3H); $^{13}$C NMR δ 141.5, 139.1, 129.8, 128.3, 127.5, 101.3 (C—I), 28.3; Phthalide (45% yield) was also isolated from the reaction mixture: $^1$H NMR δ 7.93 (d, 1H), 7.69 (m, 1H), 7.54 (m, 1H), 7.50 (d, 1H), 5.33 (s, 2H); $^{13}$C NMR δ 171.3, 146.8, 134.1, 129.2, 125.9, 122.2, 69.8.

Entry 21: 3-Iodotoluene: $^1$H NMR δ 7.56 (s, 1H), 7.50 (d, 1H), 7.13 (m, 1H), 6.99 (m, 1H), 2.31 (s, 3H); $^{13}$C NMR δ 140.3, 138.1, 134.5, 130.0, 128.4, 94.4 (C—I), 21.0.

Entry 22: 2-Methoxyiodobenzene: $^1$H NMR δ 7.77 (m, 1H), 7.31 (m, 1H), 6.83 (m, 1H), 6.71 (m, 1H), 3.88 (s, 3H); $^{13}$C NMR δ 158.1, 139.5, 129.5, 122.5, 111.0, 86.0 (C—I), 56.3. 1,3-Benzodioxan-4-one (27% yield) was also isolated from the reaction mixture: $^1$H NMR δ 7.99 (m, 1H), 7.58 (m, 1H), 7.19 (m, 1H), 7.06 (m, 1H), 5.66 (s, 2H); $^{13}$C NMR δ 161.4, 158.5, 136.3, 130.5, 123.6, 116.7, 115.0, 91.2.

Entry 23: 3-Methoxyiodobenzene: $^1$H NMR δ 7.28 (d, 1H), (m, 2H), 7.26 (d, 1H), 7.00 (t, 1H), 6.87 (dd, 1H), 3.78 (s, 3H); $^{13}$C NMR δ 160.2, 130.8, 129.9, 123.0, 113.8, 94.4 (C—I), 55.4.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. A process for the preparation of iodide, represented by scheme (1):

R—COOH→R—I     (1)

via a radical reaction, comprising visible light irradiation of a mixture of R—COOH and N-iodoamide at a temperature of between 50° C. and 200° C., wherein said N-iodoamide is mono or poly N-iodo substituted hydantoin or 3-iodo 4,4-dimethyl-2-oxazolidinone, and wherein R is saturated, linear or branched, substituted or unsubstituted alkyl; substituted or unsubstituted aryl; saturated or unsaturated, substituted or unsubstituted mono- or poly-carbocyclic or heterocyclic ring.

2. The process of claim 1, wherein said substituted hydantoin is 5,5-dimethylhydantoin, 3-benzyl-5,5-dimethylhydantoin, 5-methyl-5-phenylhydantoin, 5,5-diphenylhydantoin, 5,5-hexamethylenehydantoin, 5,5-pentamethylenehydantoin or 5,5-tetramethylenehydantoin.

3. The process of claim 2, wherein said mono or poly N-iodo substituted hydantoin is 1,3-diiodo-5,5-dimethylhydantoin (DIH).

4. The process of claim 1, wherein said reacting step is conducted at a temperature of between 70° C. and 150° C.

5. The process of claim 1, wherein said reacting step is conducted in the presence of an organic solvent.

6. The process of claim 5, wherein said organic solvent is a hydrocarbon solvent, a halocarbon solvent, an ester, acetonitrile, nitromethane or any combination thereof.

7. The process of claim 6, wherein said hydrocarbon solvent is cyclohexane, heptane or benzene; said halocarbon solvent is chlorobenzene, 1,2-dichloroethane, or carbon tetrachloride; and said ester is ethyl acetate or butyl acetate.

8. The process of claim 1, wherein said R—COOH is N-protected 4-piperidinecarboxylic acid, N-protected 4-piperidineacetic acid, N-protected azetidine-3-carboxylic acid, mono-alkyl phthalate, iodobenzoic acid, bromobenzoic acid and biphenyl-4-carboxylic acid.

9. The process of claim 1, wherein said R—COOH is N-protected azetidine-3-carboxylic acid and said R—I is N-protected 3-iodoazetidine.

10. The process of claim 1, wherein said R—COOH is N-protected 4-piperidineacetic acid and said R—I is N-protected 4-(iodomethyl)piperidine.

11. The process of claim 1, wherein said R—COOH is mono-alkyl phthalate and said R—I is alkyl 2-iodobenzoate.

12. The process of claim 1, wherein said R—COOH is 2-iodobenzoic acid and said R—I is o-diiodobenzene.

13. The process of claim 1, wherein said R—COOH is biphenyl-4-carboxylic acid and said R—I is 4-iodobiphenyl.

* * * * *